United States Patent [19]

Morgan

[11] Patent Number: 5,075,232
[45] Date of Patent: Dec. 24, 1991

[54] METHOD FOR PRODUCING THE NLAVI RESTRICTION ENDONUCLEASE AND METHYLASE

[75] Inventor: Richard D. Morgan, Manchester, Mass.

[73] Assignee: New England Biolabs, Inc., Beverly, Mass.

[21] Appl. No.: 225,246

[22] Filed: Jul. 28, 1988

[51] Int. Cl.$^5$ .......................... C12N 9/22; C12N 15/55
[52] U.S. Cl. ................................ 435/199; 435/320.1; 435/252.3; 435/172.3; 536/27
[58] Field of Search ..................... 435/199, 172.3, 320, 435/252.3, 29, 73, 80, 82; 536/27

[56] References Cited

FOREIGN PATENT DOCUMENTS 0193413 3/1986 European Pat. Off. .

OTHER PUBLICATIONS

Greene, P. J. et al., (1981), J. Biol. Chem. 256(5), 2143–2153.
Newman, A. K. et al., (1981), J. Biol. Chem. 256(5), 2131–2139.
Schoner, B. et al., (1983), Gene 24, 227–236.
Walder, R. Y. (1984), J. Biol. Chem. 259(12), 8015–8026.
Gingeras et al., (1983), Proc. Nat. Acad. Sci., U.S.A. 80, 402–406.
Theriault et al., (1982), Gene 19, 355–359.
Blumenthal et al., (1985), J. Bacteriol, 164, 501–509.
Birnboin et al., (1979), Nuc. Acids Res. 7, 1513.
Szomolanyi et al., (1980), Gene 10, 219–225.
Janulaitis et al., (1982), Gene 20, 197–204.
Kiss et al., (1983) Gene 21, 111–119.
Walder et al., (1983), J. Biol. Chem. 258, 1235–1241.
Raleigh et al., (1986), Proc. Natl. Acad. Sci., U.S.A. 83, 9070–9074.
Oiang et al., (1986), Nuc. Acids. Res. 14, 1991–1999.
Borck, K. et al., (1976), Mol. Gen. Genet. 146, 199–207.
Wilson, G. G., (1988), Gene 74, 281–289.
Wilson, G. G. (1988), Tig 4(11), 314–318.
Lunnen, K. D. et al., (1988), Gene 74, 25–32.
Mann et al., (1978), Gene 3, 97–112.
Kosysh et al. (1980), Molec. Gen. Genet 178, 717–719.
Walder et al., (1981), Proc. Nat. Acad. Sci., U.S.A. 78, 1503–1507.
Bougueleret et al., (1984), Nuc. Acids Res. 12, 3659–3676.

Primary Examiner—Elizabeth C. Weimar
Assistant Examiner—Charles L. Patterson, Jr.
Attorney, Agent, or Firm—Gregory D. Williams; David G. Conlin

[57] ABSTRACT

The present invention is directed to a method for cloning and producing the NlaIV restriction endonuclease by 1) introducing the restriction endonuclease gene from *N. lactamica* NRCC 2118 into a host whereby the restriction gene is expressed; 2) fermenting the host which contains the vector encoding and expressing the NlaIV restriction endonuclease, and 3) purifying the NlaIV restriction endonuclease from the fermented host which contains the vector encoding and expressing the NlaIV restriction endonuclease activity.

7 Claims, 3 Drawing Sheets

Nla IV R+M+ clone pRM126RM122-5

☐ cloned N. lactamica DNA

—— pUC19 polylinker

METHOD FOR PRODUCING THE NlaIV RESTRICTION ENDONUCLEASE AND METHYLASE

BACKGROUND OF THE INVENTION

The present invention relates to clones for the NlaIV restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number of restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., *Gene* 3: 97–112, (1978); EcoRII: Kosykh et al., *Molec. gen. Genet* 178: 717–719, (1980); PstI: Walder et al., *Proc. Nat. Acad. Sci. USA* 78 1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E.coli* cloning plasmids (EcoRV: Bougueleret et al., *Nucleic Acids Res.* 12:3659–3676, (1984); PaeR7: Gingeras and Brooks, *Proc. Natl. Acad. Sci. U.S.A.* 80:402–406, (1983); Theriault and Roy, *Gene* 19:355–359, (1982); PvuII: Blumenthal et al., *J.Bacteriol.* 164:501–509, (1985)).

A third approach, and one that is being used to clone a growing number of systems, involves selecting for an active methylase gene; see for example U.S. patent application Ser. No. 707,079, the disclosure of which is hereby incorporated by reference herein. Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219–225, (1980); BcnI: Janulaitis et al, *Gene* 20: 197–204 (1982); BsuRI: Kiss and Baldauf, *Gene* 21: 111–119, (1983); and MspI: Walder et al., *J. Biol. Chem.* 258:1235–1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E.coli* react adversely to cytosine modification; they possess systems that destroy DNA containing methylated cytosine (Raleigh and Wilson, *Proc. Natl. Acad. Sci., USA* 83:9070–9074, (1986)). Cytosine-specific methylase genes cannot be cloned easily into these strains, either on their own, or together with their corresponding endonuclease genes. To avoid this problem it is necessary to use mutant strains of E.coli (McrA[31] and McrB-) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

The present invention relates to the type II restriction endonuclease NlaIV, which derives from *Neisseria lactamica* (NRCC 2118). NlaIV recognizes the DNA sequence 5' GGNNCC 3' and cleaves in the middle of the sequence between the two non-specified nucleotides to produce blunt ends; GGN/NCC (Qiang and Schildkraut, *Nucleic Acids Res.* 14: 1991-1999, (1986), the disclosure of which is hereby incorporated by reference herein).

SUMMARY OF THE INVENTION

In accordance with the present invention there is provided a clone containing the genes for the NlaIV restriction endonuclease and modification methylase derived from *Neisseria lactamica* (NRCC 2118), as well as related methods for the production of the enzymes. More specifically, this invention relates to clones which express the restriction endonuclease NlaIV, an enzyme which recognizes the DNA sequence 5' GGNNCC 3' and cleaves between the N nucleotides to produce flush ends.

The preferred method for cloning this enzyme comprises forming a library containing the DNA from *N. lactamica* (NRCC 2118), isolating those clones which contain DNA coding for the NlaIV modification methylase and screening among these to identify those that also contain the NlaIV restriction endonuclease gene.

DETAILED DESCRIPTION OF THE INVENTION

The present invention relates to clones of the NlaIV restriction and modification genes, as well to the restriction endonuclease NlaIV produced from such clones. The NlaIV genes are cloned by a method which takes advantage of the fact that certain clones which are selected on the basis of containing and expressing the NlaIV modification methylase gene also contain the NlaIV restriction gene. The DNA of such clones is resistant to digestion, in vitro, by the NlaIV restriction endonuclease. This resistance to digestion affords a means for selectively isolating clones encoding the NlaIV methylase and restriction endonuclease.

Figure 1:
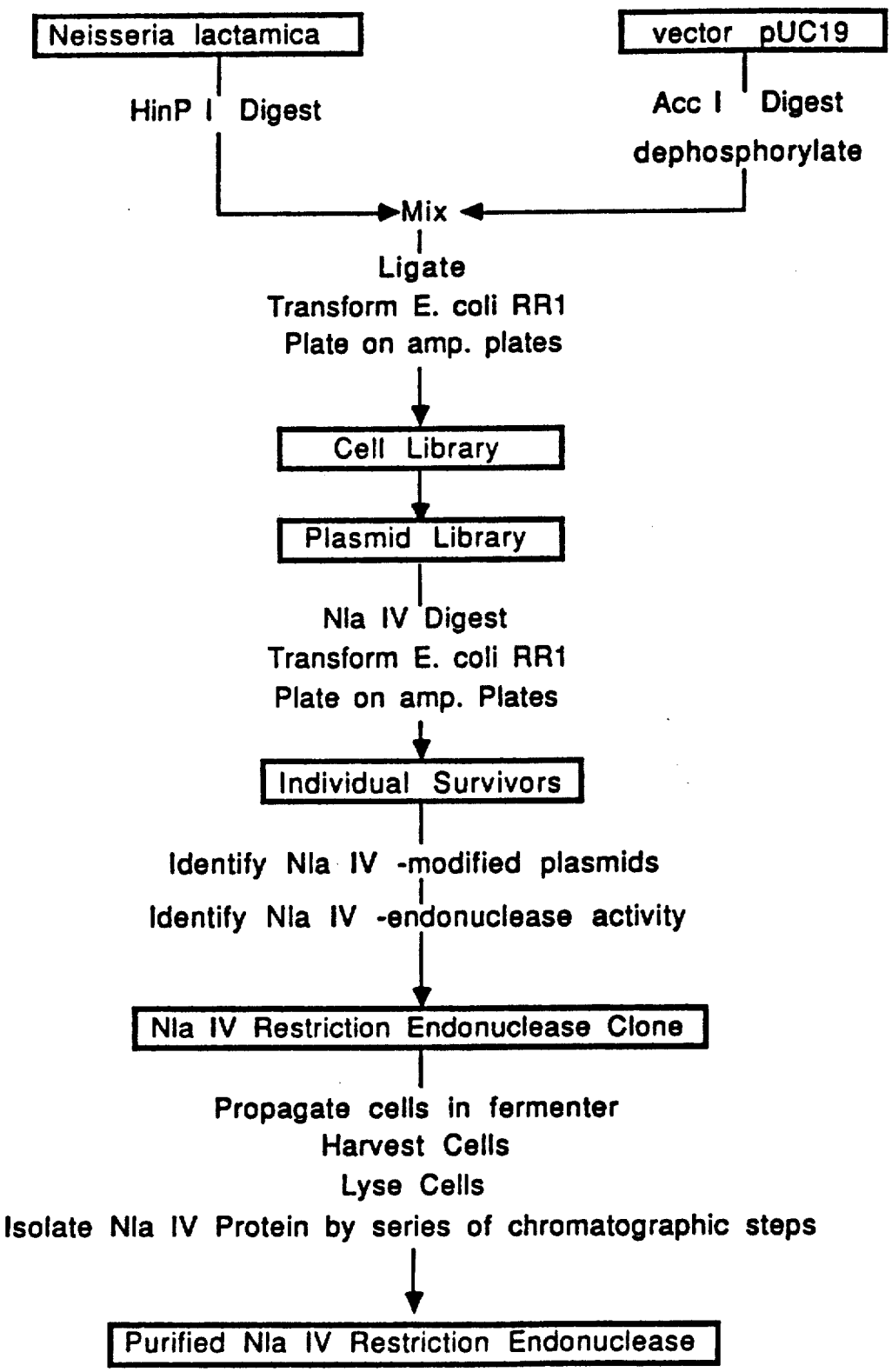
FIG. 1 illustrates the scheme for cloning and producing the NlaIV restriction endonuclease.

The method described herein by which the NlaIV restriction gene and methylase gene are preferably cloned and expressed are illustrated in FIG. 1, and they include the following steps:

1. The DNA of *Neisseria lactamica* is purified.
2. The DNA is digested with a restriction endonuclease such as HinPI.
3. The digested DNA is ligated to a cloning vector such as pUC19 (ATCC 37254), that contains one or more NlaIV sites. The ligated DNA is transformed into an appropriate host such as *Escherichia coli* strain RR1 (ATCC 31343).
4. The transformed mixture is plated onto media selective for transformed cells, such as the antibiotic ampicillin. After incubation, the transformed colonies are collected together into a single culture, the cell library.
5. The recombinant plasmids are purified in toto from the cell library to make the plasmid library.
6. The plasmid library is digested to completion with the NlaIV restriction endonuclease, prepared from *N. lactamica* by standard protein purification techniques. NlaIV digestion differentially destroys unmodified, non-methylase-containing, clones, increasing the relative frequency of NlaIV methylase clones.
7. The digested plasmid library is transformed back into an appropriate host such as *E.coli* RR1, and transformants are recovered by plating onto selective media. The colonies are picked and their DNA is analyzed for the presence of the NlaIV modification gene: the plasmids that they carry are purified and incubated with the NlaIV restriction endonuclease to determine whether they are resistant to digestion. Total cellular DNA (chromosomal and plasmid) is also purified and incubated with the NlaIV restriction endonuclease. The DNA of clones that carry the NlaIV modification gene should be fully modified, and both plasmid DNA and total DNA should be substantially resistant to digestion.
8. Clones carrying the NlaIV restriction endonuclease are identified by preparing cell extracts of the NlaIV methylase clones, identified in step 8, and assaying the extracts for NlaIV restriction endonuclease activity.
9. The NlaIV restriction endonuclease may be produced from clones carrying the NlaIV restriction and modification genes by propagation in a fermenter in a rich medium containing ampicillin. The cells are collected by centrifugation and disrupted by sonication to produce a crude cell extract containing the NlaIV restriction endonuclease activity.
10. The crude cell extract containing the NlaIV restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of NlaIV Restriction Endonuclease Gene

1. DNA purification: 5 g of frozen *Neisseria lactamica* (NRCC 2118) cells were resuspended in 20 ml of 25% sucrose, 50 mM Tris pH 8.0. 10 ml of 0.25M EDTA pH 8.0, and 6 ml of 10 mg/ml lysozyme in 0.25M Tris pH 8.0 were added. The suspension was kept on ice for 16 hours, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 60 ml of Chloroform. The emulsion was centrifuged at 10K rpm for 30 minutes to separate the phases. The viscous upper phase was dialyzed against four changes of DNA buffer (10 mM Tris pH 8.0, 1 mM EDTA). The dialyzed solution was then digested with RNase at a final concentration of 100 ug/ml for 2 hours at 37° C. The DNA was then precipitated by the addition of 5M NaCl to a final concentration of 0.4M, and 0.55 volumes of isopropyl alcohol. The precipitated DNA was spooled onto a glass rod, air-dried, then dissolved in DNA buffer to a concentration of approximately 350 ug/ml and stored at 4° C.

2. Digestion of DNA: 50 ug of *N. lactamica* DNA was diluted into 500 ul of HinPI restriction endonuclease digestion buffer (10 mM Tris pH 8.0, 10 mM $MgCl_2$, 50 mM NaCl). A serial dilution of HinPI restriction endonuclease from 4 units/ug to 0.06 units/ug was performed and the solutions were incubated at 37° C. for 1 hr. The extent of HinPI digestion was analyzed by gel electrophoresis of a small aliquot from each dilution. The dilutions which produced a range of fragments of the desired size (2 Kb-15 Kb) were then pooled and extracted with an equal volume of equilibrated phenol, followed by two extractions with chloroform. The DNA was precipitated by the addition of 5M NaCl to a final concentration of 0.4M and 0.55 volumes of isopropyl alcohol. The DNA was then dissolved in DNA buffer to a concentration of approximately 100 ug/ml.

3. Ligation and transformation: 6 ug (60 ul) of HinPI-digested *N. lactamica* DNA was mixed with 3 ug (15 ul) of AccI-cleaved and dephosphorylated pUC19 (ATCC 37254). 20 ul of 10× ligation buffer (500 mM Tris pH 7.5, 100 mM $MgCl_2$, 100 mM DTT, 5 mM ATP), and 105 ul of sterile distilled water were added to bring the volume to 200 ul. 7.5 ul (3000 NEB units) of T4 DNA ligase was added and the solution was incubated at 17° C. for 16 hours. The solution was sterilized by extraction with 20 ul of chloroform, then clarified by microcentrifugation for 15 seconds. 62.5 ul of the ligation solution was mixed with 500 ul of $SSC/CaCl_2$ (50 mM NaCl, 5 mM $Na_3$Citrate, 67 mM $CaCl_2$) and 1.0 ml of ice-cold, competent *E.coli* RR1 (ATCC 31343) cells were added. The solution was incubated at 42° C. for 4 minutes, then 10 ml of Luria-broth (L-broth) was added and incubation was continued at 37° C. for 3 hr.

4. Cell Library: The transformed culture was gently centrifuged, the supernatant was discarded and the cells were resuspended in 1.0 ml of L-broth. 200 ul portions of the resuspended cells were plated onto Luria-agar (L-agar) plates containing 100 ug/ml ampicillin. The plates were incubated overnight at 37° C. The transformed cells that grew up on the surfaces of the plates were collected together by flooding each of the plates with 2.5 ml of 10 mM Tris pH 7.5, 10 mM $MgCl_2$, scraping the colonies together, and pooling the suspensions into a single tube.

5. Plasmid Library: 2.0 ml of the cell library was inoculated into 500 ml of L-broth containing 100 ug/ml ampicillin. The culture was shaken overnight at 37° C. then centrifuged at 5K rpm for 5 minutes. The supernatant was discarded and the cell pellet was resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris pH 8.0 were added. The solution was kept on ice for 1 hour, then 12 ml of 1% Triton X-100, 50 mM Tris pH 8.0, 67 mM EDTA was added and the suspension was gently swirled to induce cell lysis.

The lysed mixture was transferred to a 50 ml tube and centrifuged for 45 minutes at 17K rpm, 4° C. The supernatant was removed with a pipette. 20.0 gm of solid CsCl was weighed into a 50 ml plastic screw-cap tube and 22.0 gm of supernatant was pipetted into the tube and mixed. 0.5 ml of 10 mg/ml ethidium bromide in 10 mM Tris pH 8.0, 100 mM NaCl, 1 mM EDTA was added. The solution was transferred to two ⅝ in. ×3 in. centrifuge tubes and spun in a Beckman Ti70 rotor for 30 hours at 50K rpm, 17° C. To collect the plasmids, the tubes were opened, illuminated with ultraviolet light, and the lower of the two fluorescent bands was collected by syringe. The lower band from each tube was combined and the ethidium bromide was removed by extracting three times with an equal volume of water-saturated, $CsCl_2$ saturated isopropyl alcohol.

The extracted solution was diluted with four volumes of DNA buffer, then the nucleic acid was precipitated by the addition of 2 volumes of isopropanol. The solution was placed at −70° C. for 30 minutes then centrifuged for 15 minutes at 15K rpm, 4° C. The supernatant was discarded, the pellet was air-dried for 30 minutes then dissolved in 1 ml of 10 mM Tris pH 8.0, 1 mM EDTA and stored at 4° C. The plasmid DNA concentration was found to be approximately 200 ug/ml.

6. Digestion of the Plasmid Library: 4 ug (20 ul) of the plasmid library was diluted into 100 ul of NlaIV restriction endonuclease digestion buffer (10 mM Tris pH 7.4, 10 mM $MgCl_2$, 10 mM 2-mercaptoethanol, 50 mM $(NH4)2SO4$). 8 units (8 ul) of NlaIV restriction endonuclease were added and the tube was incubated at 37° C. for 2 hours. The reaction was sterilized by extraction with 20 ul chloroform, then clarified by microcentrifugation for 15 seconds.

7. Transformation: 20 ul (0.8 ug) of the digested library was mixed with 100 ul of $SSC/CaCl_2$ (section 3) and 200 ul of ice-cold, competent, *E.coli* RR1. The mixture was warmed to 42° C. for 3 minutes and then plated onto an L-agar containing 100 ug/ml ampicillin. The plate was incubated overnight at 37° C. NlaIV digestion reduced the number of transformants $10^4$-fold compared with transformation by undigested plasmids. Nine colonies grew following the NlaIV digestion; each was inoculated into 10 ml of L-broth containing ampicillin, to prepare a miniculture, and streaked onto an L-agar plate containing ampicillin, to prepare a master stock.

8. Analysis of surviving individuals: The nine surviving colonies obtained from section 7 were grown into 10 ml cultures and the plasmids that they carried were prepared by the following miniprep purification procedure, adapted from the method of Birnboin and Doly, *Nucleic Acids Res.* 7: 1513 (1979).

Miniprep Procedure: Each culture was centrifuged at 8K rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15K rpm, 4° C. for 10 minutes. Each supernatant was poured into a centrifuge tube containing 3 ml of isopropanol and mixed. After 10 minutes at room temperature, the tubes were spun at 15K rpm for 10 minutes to pellet the precipitated nucleic acids. The supernatants were discarded and the pellets were air-dried at room temperature for 30 minutes. Once dry, the pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 2 minutes and the supernatants discarded. The pellets were air-dried at room temperature for 30 minutes, then redissolved in 150 ul of 10 mM Tris 1 mM EDTA, pH 8.0. The plasmid minipreps were subsequently analyzed by digestion with NlaIV and HinPI.

Figure 2:
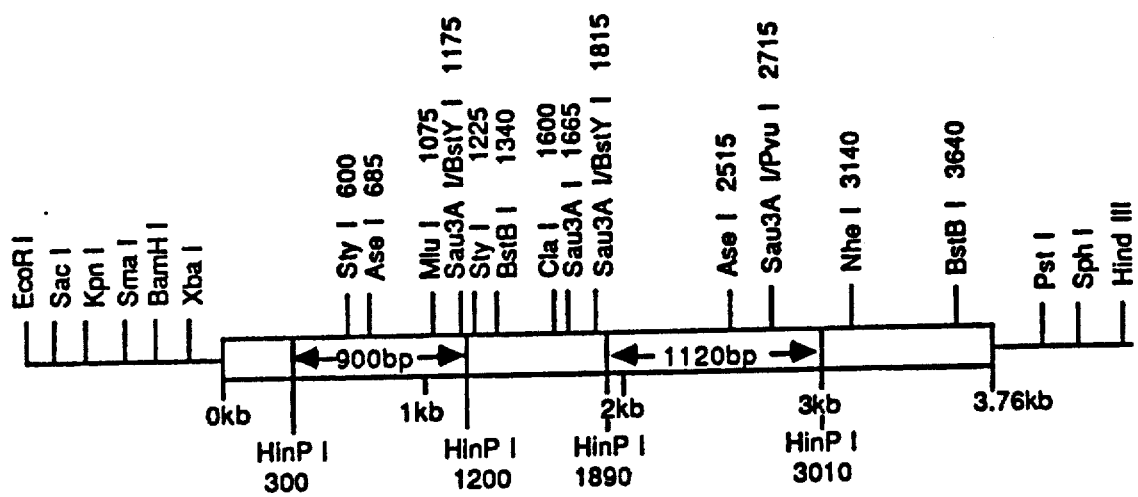
FIG. 2 is a restriction map of a 3.8 Kb HinPI fragment of *N. lactamica* DNA that encodes the NlaIV restriction endonuclease and modification methylase. The fragment was cloned into the AccI site of pUC19(ATCC 37254) to create pRM126RM 122-5.
Figure 3:
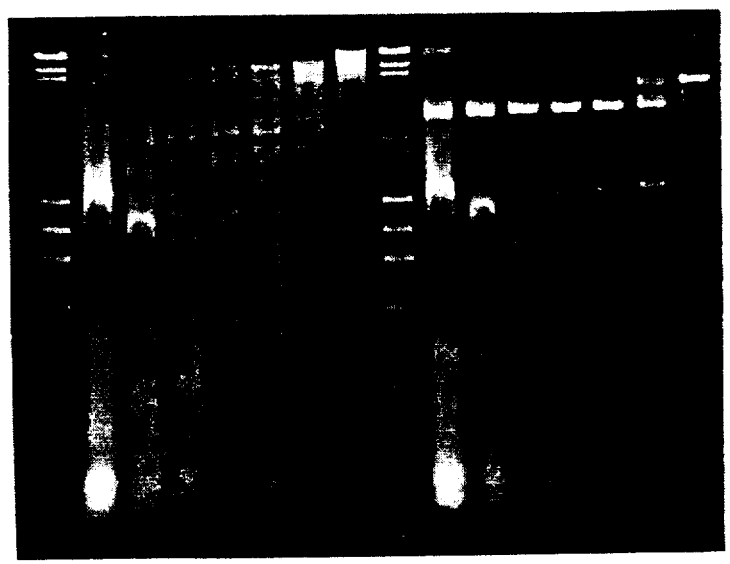
FIG. 3 is a photograph of an agarose gel demonstrating NlaIV restriction endonuclease activity in cell extracts of *E.coli* RR1 (ATCC 31343) carrying pRM126RM 122-5.

9. NlaIV Methylase Gene Clones: One of the 9 plasmids that were analyzed was found to be sensitive to NlaIV digestion and to carry diverse HinPI fragments of *N. lactamica* DNA. This plasmid was spurious and was discarded. The remaining 8 plasmids were found to be resistant to NlaIV digestion and to carry a 1.12 Kb and a 0.90 Kb HinPI fragment in common. All of the plasmids carried additional common fragments, presumably chromosomal neighbors of the 1.12 and 0.90 Kb fragments. Four different plasmid constructs were obtained and were found to produce approximately the same amount of Nla IV endonuclease. The clone pRM126RM 122-5 was chosen for detailed analysis (FIG. 2) because it contained the smallest amount of *N. lactimica* DNA; 3.8 Kb. A sample of pRM126RM 122-5 has been deposited at the American Type Culture Collection under ATCC Accession No. 40882. Other R+M+ clones ranged in size from 4.8 Kb (pRM126RM 122-7) to 6.3 Kb (pRM126RM 122-8) and, each contained at least 2.8 Kb of *N. lactamica* DNA in common with pRM126RM 122-5.

10. NlaIV Restriction Gene Clone: pRM126RM 122-5, and similar plasmids, were found to encode and express the NlaIV restriction endonuclease by assaying extracts of *E.coli* RR1 that carried the plasmids.

Endonuclease Assay

A 250 ml culture of the cells to be assayed was grown overnight at 37° C. in L-broth containing 100 ug/ml ampicillin. The culture was centrifuged at 8K rpm for 5 minutes and the cell pellet was resuspended in 10 ml of 10 mM Tris-HCl pH 7.5, 10 mM 2-mercaptoethanol, 1 mM $MgCl_2$. 1.5 ml of the suspension was sonicated gently for three 15-second bursts to disrupt the cells. The sonicated extract was microcentrifuged for 5 min to remove cell debris and the supernatant was assayed for endonuclease activity in the following way:

8 ug (8 ul) of purified phage phiX174 RFI DNA was diluted into 400 ul of NlaIV restriction endonuclease digestion buffer (section 6). The solution was dispensed into 7 tubes, 75 ul into the first tube and 50 ul into each of the remaining 6 tubes. 13.5 ul of the extract was added to the first tube to achieve 9 ul extracting DNA. 25 ul was then removed from the first tube and transferred to the second tube to achieve 3 ul/ug. 25ul serial transfers were continued into tubes 3 (1 ul/ug), 4 (0.3 ul/ug), 5 (0.1 ul/ug), 6 (0.03 ul/ug) and 7 (0.01 ul/ug). The tubes were incubated at 37° C. for one hour, then 20 ul from each was analyzed by gel electrophoresis. The extract was found to contain approximately $1 \times 10^3$ units of NlaIV restriction endonuclease per ml, which corresponds to about $1 \times 10^4$ units per gram of cells.

11. *E.coli* RR1 carrying pRM126RM 122-5 is the preferred host from which the NlaIV restriction endonuclease can be purified. The strain should be grown to stationary phase at 37° C. in a fermenter, in L-broth containing ampicillin. The cells should then be collected by centrifugation and either broken immediately for extract preparation, or stored frozen at −70° C. until it is convenient to do so.

What is claimed is:

1. Isolated DNA coding for the NlaIV restriction endonuclease, wherein the isolated DNA is obtainable from the vector pRM126RM 122-5.

2. A recombinant DNA vector comprising a vector into which a DNA segment coding for the NlaIV endonuclease has been inserted.

3. Isolated DNA coding for the NlaIV restriction endonuclease and methylase, wherein the isolated DNA is obtainable from the vector pRM126RM 122-5.

4. A cloning vector which comprises the isolated DNA of claim 3.

5. The cloning vector of claim 4, wherein the cloning vector comprises pRM126RM 122-5.

6. A host cell transformed by the vector of claim 2, 3 or 5.

7. A method of producing an NlaIV restriction endonuclease comprising culturing a host cell transformed with the vector of claim 2, 3 or 5 under conditions suitable for the expression of said endonuclease.

* * * * *

UNITED STATES PATENT AND TRADEMARK OFFICE
CERTIFICATE OF CORRECTION

PATENT NO. : 5,075,232
DATED : December 24, 1991
INVENTOR(S) : Richard D. Morgan It is certified that error appears in the above-indentified patent and that said Letters Patent is hereby corrected as shown below:

On title page, item [54] "NLAVI" should read --NLAIV--

Column 1, line 2, "NLAVI" should read --NLAIV--

Column 4, line 20, replace "in toto" with --in toto--

Signed and Sealed this

First Day of March, 1994

Attest:

BRUCE LEHMAN

Attesting Officer

Commissioner of Patents and Trademarks